United States Patent [19]
Schropp

[11] 3,962,074
[45] June 8, 1976

[54] PROCESS FOR SEPARATING ACRYLIC ACID FROM AQUEOUS SOLUTIONS

[75] Inventor: Wilhelm Karl Schropp, Luetzelsachsen, Germany

[73] Assignee: BASF Aktiengesellschaft, Ludwigshafen (Rhine), Germany

[22] Filed: May 6, 1974

[21] Appl. No.: 467,255

[30] Foreign Application Priority Data
May 9, 1973 Germany............................ 2323328

[52] U.S. Cl............................... 210/21; 260/643 D; 260/705
[51] Int. Cl.²......................................... B01D 11/04
[58] Field of Search ............. 210/21; 260/530, 533, 260/643 D, 705

[56] References Cited
UNITED STATES PATENTS
3,809,645  5/1974  Matsuzawa et al. ................... 210/21

*Primary Examiner*—Frank A. Spear, Jr.
*Attorney, Agent, or Firm*—Johnston, Keil, Thompson & Shurtleff

[57] ABSTRACT

Acrylic acid is separated from aqueous solution by extraction of the solutions with organic solvents and separating the organic phase from the aqueous raffinate. Extraction is effected with a mixture of from 1 to 50 parts by weight of butanol and from 1 to 10 parts by weight of butyl acrylate.

6 Claims, No Drawings

PROCESS FOR SEPARATING ACRYLIC ACID FROM AQUEOUS SOLUTIONS

This invention relates to a process for separating acrylic acid from aqueous solutions by extracting said solutions with specific organic solvents.

In the esterification of acrylic acid with alkanols such as n-butanol, isobutanol and 2-ethylhexanol complete conversion is not generally obtained. Thus, in order to avoid the passage of unreacted acrylic acid to public waters via the waste water, the acrylic acid must be separated from the waste esterification liquors.

A number of solvents have already been proposed for the extraction of acrylic acid from aqueous solutions, for example ethyl acetate, ethyl acrylate, methyl isobutyl ketone, 2-ethylhexanol and n-butyl acrylate. In the separation of acrylic acid from waste esterification liquors, the concentration of the acrylic acid in the waste liquors is generally in the range 2 to 5% by weight. The concentration of acrylic acid in aqueous solutions such as occur in some processes for the manufacture of acrylic acid by oxidation of propylene or acrolein is usually higher, i.e. generally from 10 to 20% by weight.

If the acrylic acid extracted from the aqueous solution by a solvent is to be passed to an esterification process, it is advisable to effect the extraction with a solvent which is itself present in the said esterification process, since, if this were not the case, it would be necessary to separate the solvent and this would give rise to additional cost. Thus for example, 2-ethylhexanol and n-butyl acrylate are suitable solvents in some cases since they are either reactants or reaction products and make it possible to return the extract directly to the esterification reaction involved.

However, 2-ethylhexanol and n-butyl acrylate suffer from the drawback that they have only a moderate solvent action on acrylic acid, which means that the cost of extraction is relatively high. n-Butyl acrylate has the further disadvantage that, being a reaction product, it adversely influences the equilibrium of the esterification reaction, which means either that a lower conversion must be accepted or that the esterification apparatus must be enlarged.

If n-butanol is used in place of butyl acrylate for the extraction of acrylic acid from aqueous solutions thereof, this solvent may also be returned to the esterification reaction of acrylic acid to butyl acrylate, but phase-mixing occurs in the neutralized waste liquor in the region of industrially interesting solvent proportions, this presumably being due to the salts present in the reaction mixture.

I have now found that acrylic acid may be extracted from aqueous solutions by means of organic solvents in a particularly advantageous manner if the aqueous acrylic acid solution is extracted with a mixture of from 1 to 50 parts by weight of butanol and from 1 to 10 parts by weight of butyl acrylate. The aqueous solutions to be fed to the extraction stage should contain the acrylic acid in free form, i.e., alkaline waste liquors or neutralized waste liquors from esterification reactions are advantageously acidified prior to extraction, for which purpose it is preferred to use nonoxidizing acids such as sulfuric acid or hydrochloric acid in amounts sufficient to liberate all of the acrylic acid.

The ratio of butanol to butyl acrylate should be from 1-10:1-3 parts by weight, because the cost of extraction is particularly low within this range. For example, mixtures of n-butanol and n-butyl acrylate containing up to 30% of their weight of n-butyl acrylate are very superior to n-butanol alone. Butyl acrylate/butanol mixtures of this kind extract acrylic acid in a much more effective manner than either butyl acrylate or butanol alone.

In some cases, the butanol/butyl acrylate mixtures used in our novel process for the extraction of aqueous acrylic acid solutions may be those obtained in the manufacture of butyl acrylate by the esterification of acrylic acid with butanol, such as when excess butanol is removed from the reaction mixture and worked up. In this case, the butanol/butyl acrylate mixtures may contain other components including by-products of the esterification and small amounts of impurities. The butanol/butyl acrylate mixtures usually contain water as a further component. They are preferably used in the form of mixtures saturated with water at the temperature of extraction.

The process of the invention is particularly interesting for the extraction of acidified waste liquors obtained in the neutral state in the manufacture of acrylates. The concentration of acrylic acid in such waste liquors is generally from 2 to 15% by weight. However, our novel process is also suitable for extracting aqueous acrylic acid solutions from other sources and containing up to 20% by weight or more of acrylic acid. The process is also suitable for extraction of aqueous acrylic acid solutions as sometimes occur in the manufacture of acrylic acid by the oxidation of propylene or acrolein.

The acrylic acid extracted in our novel process in the form of a mixture with butanol and butyl acrylate may be generally fed in this form to a process for the manufacture of butyl acrylate by the esterification of acrylic acid with butanol. In some cases, particularly when the acrylic acid content is high, it may be advantageous to separate the water present in the mixture by azeotropic distillation.

When carrying out the process, the amount of butanol/butyl acrylate mixture relative to aqueous acrylic acid solution may be varied within wide limits. In general, from 0.2 to 3 kg and preferably from 0.25 to 1 kg of butanol/butyl acrylate mixture (calculated as non-aqueous) are used per kg of aqueous acrylic acid solution. Extraction is generally carried out at room temperature, particularly at temperatures ranging from 10° to 35°C, although it is possible in some cases to operate at lower or higher temperatures, e.g. at 0°C or at from 40° to 60°C.

Our novel process may be carried out by essentially all extraction technique, although we prefer to use a continuous countercurrent technique. The process has been successfully executed using for example sieve plate columns, packed columns and columns having rotating baffles and also extracting apparatus operating on the mixer-settler principle.

Since both acrylic acid and butyl acrylate polymerize very easily, the process is preferably carried out with the addition of conventional stabilizers such as hydroquinone, hydroquinone monomethyl ether, methylene blue and/or phenothiazine.

In the following Examples the parts and percentages are by weight. In these Examples, a column packed with Raschig rings and having an efficiency of approximately four theoretical trays is used.

EXAMPLE 1 a. 300 parts of an acidified aqueous waste esterification liquor having an acrylic acid content of 6.4% are extracted with 100 parts of a mixture of 73.8% of n-butanol, 8.2% of n-butyl acrylate and 18% of water by feeding the aqueous acrylic acid solution to the top and the solvent mixture to the bottom of the column. The temperature in the column is 25°C.

Gas chromatographic analysis of the aqueous raffinate shows less than 100 ppm of acrylic acid. The extraction efficiency is greater than 99.8%.

b. If, in place of the butanol/butyl acrylate mixture, use is made of an equal weight of butyl acrylate alone, the extraction efficiency based on acrylic acid is only 80% under otherwise identical conditions.

c. If, in place of the butanol/butyl acrylate mixture, use is made of an equal amount of butanol alone, phase-mixing occurs. If 7% acrylic acid solution in water is used, the extraction efficiency is 99.5%.

EXAMPLE 2

In the manner described in Example 1, 300 parts of a waste liquor containing 6.2% of acrylic acid, which has been obtained by neutralization and has been acidified with sulfuric acid, are extracted with 100 parts of a mixture of 64.3% of n-butanol, 16.1% of n-butyl acrylate and 12.5% of water at 20°C.

The extraction efficiency, based on acrylic acid, is in this case more than 99.8%. The acrylic acid extract, which contains butanol and butyl acrylate and water in addition to the acrylic acid, may be fed to an esterification reaction which butanol is esterified with acrylic acid to form butyl acrylate.

I claim:

1. In a process for extracting acrylic acid from an aqueous solution thereof which comprises extracting said solution with an organic solvent and separating the organic phase from the aqueous raffinate, the improvement wherein the aqueous acrylic acid solution is extracted with a mixture of butanol and butyl acrylate, which mixture is saturated with water and in which mixture the weight ratio of butanol to butyl acrylate is from 1:3 to 10:1.

2. A process as claimed in claim 1 wherein said butanol is n-butanol and said butyl acrylate is n-butyl acrylate.

3. In a process for extracting acrylic acid from an aqueous solution thereof by extracting said solution with an organic solvent and separating the organic phase from the aqueous raffinate, the improvement wherein the aqueous acrylic acid solution is extracted at room temperature with a water saturated mixture of butanol and butyl acrylate in an amount of from 0.2 to 3 kg of said mixture (calculated as non-aqueous) per kg of said aqueous acrylic acid solution, the weight ratio of butanol to butyl acrylate being from 1:3 to 10:1.

4. A process as claimed in claim 3 wherein said butanol is n-butanol and said butyl acrylate is n-butyl acrylate.

5. In a process for extracting acrylic acid from an aqueous solutions thereof by extracting said solution with an organic solvent and separating the organic phase from the aqueous raffinate, the improvement wherein the aqueous acrylic acid solution is extracted at 10° to 35°C with a water saturated mixture of butanol and butyl acrylate in an amount of from 0.2 to 3 kg of said mixture (calculated as non-aqueous) per kg of said aqueous acrylic acid solution, the weight ratio of butanol to butyl acrylate being from 1:3 to 10:1.

6. A process as claimed in claim 5 wherein said butanol is n-butanol and said butyl acrylate is n-butyl acrylate.

* * * * *